(12) United States Patent
Kim et al.

(10) Patent No.: US 9,797,837 B2
(45) Date of Patent: Oct. 24, 2017

(54) DETECTOR AND DETECTION METHOD

(71) Applicant: The University of Tokyo, Tokyo (JP)

(72) Inventors: Soo Hyeon Kim, Tokyo (JP); Hiroyuki Noji, Tokyo (JP); Ryota Iino, Tokyo (JP); Jun Ohta, Ikoma (JP); Takashi Tokuda, Ikoma (JP); Kiyotaka Sasagawa, Ikoma (JP); Toshihiko Noda, Ikoma (JP)

(73) Assignee: The University of Tokyo, Tokyo (JP)

( * ) Notice: Subject to any disclaimer, the term of this patent is extended or adjusted under 35 U.S.C. 154(b) by 56 days.

(21) Appl. No.: 14/423,771

(22) PCT Filed: Aug. 29, 2013

(86) PCT No.: PCT/JP2013/073147
§ 371 (c)(1),
(2) Date: Feb. 25, 2015

(87) PCT Pub. No.: WO2014/034781
PCT Pub. Date: Mar. 6, 2014

(65) Prior Publication Data
US 2015/0204785 A1    Jul. 23, 2015

(30) Foreign Application Priority Data
Aug. 31, 2012   (JP) .................................. 2012-191513

(51) Int. Cl.
*G01N 21/63* (2006.01)
*B01L 3/00* (2006.01)
(Continued)

(52) U.S. Cl.
CPC ...... *G01N 21/6428* (2013.01); *B01L 3/50853* (2013.01); *B01L 3/502769* (2013.01);
(Continued)

(58) Field of Classification Search
CPC .. G01N 21/6428; G01N 21/636; G01N 21/63; G01N 21/62; B01L 3/502769;
(Continued)

(56) References Cited

U.S. PATENT DOCUMENTS

2004/0029203 A1   2/2004 Gumbrecht et al.
2006/0264779 A1* 11/2006 Kemp .................. A61B 5/1411
                                                       600/583
(Continued)

FOREIGN PATENT DOCUMENTS

JP       2008-544214 A    12/2008
JP          4347564 B2    10/2009
(Continued)

OTHER PUBLICATIONS

Soo Hyeon Kim et al., "Large-scale femtoliter droplet array for digital counting of single biomolecules", Lab Chip, vol. 12, Jan. 1, 2012, pp. 4986-4991.
(Continued)

*Primary Examiner* — Christine T Mui
(74) *Attorney, Agent, or Firm* — Locke Lord LLP; Howard M. Gitten

(57) ABSTRACT

There are provided a detector and a detection method capable of detecting a biological sample with high sensitivity. A detector is provided with a microchamber array including a plurality of storage sections to be filled with a hydrophilic solvent containing a biological sample; and an image sensor in which picture elements are disposed corresponding to the storage sections, wherein the microchamber array includes a flow channel in communication with openings of the storage sections; a hydrophobic solvent supply unit arranged in continuity with the flow channel; and a through-hole which allows the hydrophilic solvent to enter and exit the flow channel, and the hydrophobic solvent
(Continued)

supply unit flows a hydrophobic solvent into the flow channel by an externally-applied force.

14 Claims, 11 Drawing Sheets

(51) Int. Cl.
*G01N 21/64* (2006.01)
*G01N 15/14* (2006.01)
*G01N 15/10* (2006.01)

(52) U.S. Cl.
CPC .. *G01N 21/6454* (2013.01); *B01L 2200/0673* (2013.01); *B01L 2300/041* (2013.01); *B01L 2300/0636* (2013.01); *B01L 2300/0654* (2013.01); *B01L 2300/0819* (2013.01); *B01L 2400/0481* (2013.01); *G01N 15/1463* (2013.01); *G01N 2015/1006* (2013.01); *G01N 2021/6439* (2013.01); *Y10T 436/143333* (2015.01)

(58) Field of Classification Search
CPC .... B01L 3/5027; B01L 3/502; B01L 3/50853; B01L 3/5085; B01L 3/508; B01L 3/50
USPC ........ 436/172, 164, 401, 400, 547; 422/401, 422/400, 547, 172, 164
See application file for complete search history.

(56) References Cited

U.S. PATENT DOCUMENTS

| | | |
|---|---|---|
| 2007/0298975 A1 | 12/2007 | Ihama et al. |
| 2010/0252128 A1 | 10/2010 | Gong et al. |
| 2010/0323926 A1 | 12/2010 | Lee et al. |

FOREIGN PATENT DOCUMENTS

| | | |
|---|---|---|
| JP | 2010-533860 A | 10/2010 |
| JP | 2011-506998 A | 3/2011 |
| JP | 4909656 B2 | 4/2012 |
| WO | WO-01/55704 A1 | 8/2001 |
| WO | WO-2010/091246 A2 | 8/2010 |
| WO | WO-2011/160430 A1 | 12/2011 |

OTHER PUBLICATIONS

Extended European Search Report dated Mar. 8, 2016, issued for the European patent application No. 13834082.3.
Kiyotaka Sasagawa et al., "Complementary Metal-Oxide-Semiconductor Image Sensor with Microchamber Array for Fluorescent Bead Counting," Japanese Journal of Applied Physics, 51 (2012) pp. 02BL01-1 to 02BL01-4 and a cover page.
International Search Report dated Oct. 22, 2013, issued for PCT/JP2013/073147.

* cited by examiner

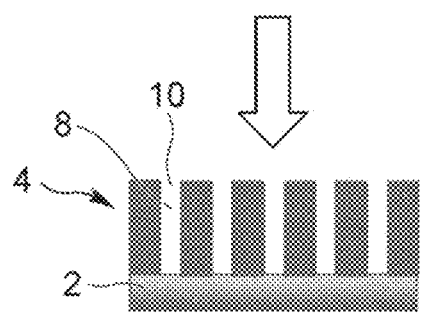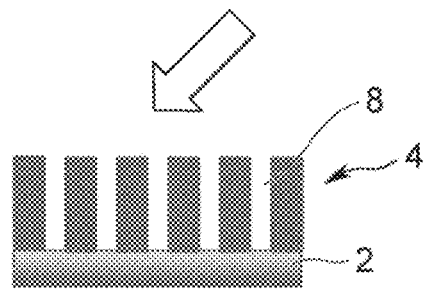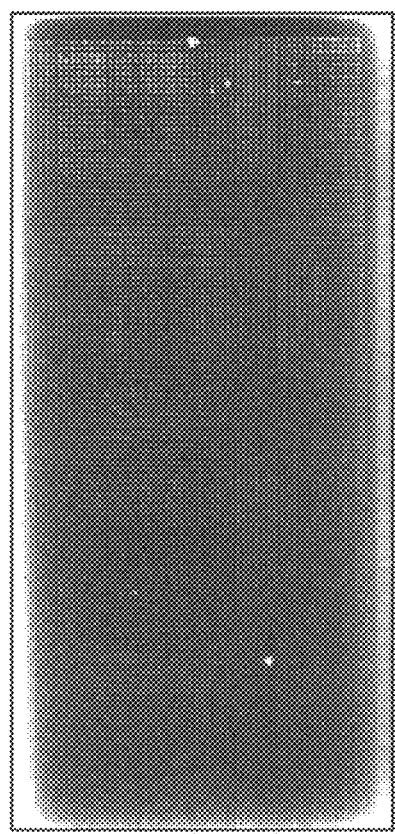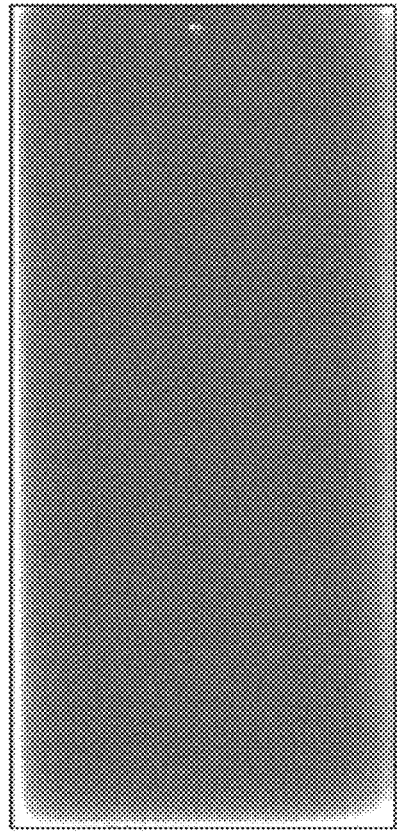
FIG. 7A　　　　　　　　FIG. 7B

DETECTOR AND DETECTION METHOD

TECHNICAL FIELD

The present invention relates to a detector and a detection method, and particularly, to an apparatus capable of detecting biological samples.

BACKGROUND ART

Since it has been possible to directly observe the movement of individual biological samples, such as live (having activity) protein and nucleic acid, using an optical microscope, there has been adopted a method for examining the molecular-level functionality and activity of each biological sample primarily by means of optical microscope-based measurement. In order to identify individual molecules targeted for examination, a reagent composed of a fluorescent dye, a gold colloid or microparticles (polystyrene beads, magnetic bead, or the like) is attached to those molecules to visualize the presence of molecules having sizes invisible with the resolution of an optical microscope.

The above-described method requires a large-scale, expensive optical microscope, however. In addition, the method requires direct observation of the biological samples to count the presence thereof. The method thus has the problem of being not capable of conducting examinations at high speeds and with ease.

On the other hand, there is disclosed a detector for biological samples provided with a microchamber array including a plurality of storage sections for containing a biological sample, and a CMOS image sensor including picture elements disposed corresponding to the respective storage sections (see, for example, Non-Patent Literature 1).

CITATION LIST

Non-Patent Literature

Non-Patent Literature 1: Complementary Metal-Oxide-Semiconductor Image Sensor with Microchamber Array for Fluorescent Bead Counting, Kiyotaka Sasagawa, et al., JAPANESE JOURNAL OF APPLIED PHYSICS, 51 (2012) 02BL01

SUMMARY OF INVENTION

Technical Problem

In Non-Patent Literature 1 cited above, however, the openings of all of the storage sections are in communication with one another through a flow path. Consequently, the detector is problematic in that the concentrations of the biological sample and the reagent contained in the storage sections become lower, and therefore, measurement sensitivity degrades.

Hence, it is an object of the present invention to provide a detector and a detection method capable of detecting biological samples with high sensitivity.

Solution to Problem

A detector according to the present invention is provided with a microchamber array disposed inside a main unit and including a plurality of storage sections to be filled with a hydrophilic solvent containing a biological sample; and an image sensor in which picture elements are disposed corresponding to the storage sections, wherein the main unit includes a flow channel in communication with openings of the storage sections; a hydrophobic solvent supply unit arranged in continuity with the flow channel; and a through-hole through which the hydrophilic solvent can enter and exit the flow channel, surfaces of the microchamber array have hydrophobicity, and the hydrophobic solvent supply unit causes a hydrophobic solvent to flow into the flow channel by an externally-applied force.

A detection method according to the present invention includes the steps of filling a hydrophilic solvent containing a biological sample into a plurality of storage sections of a microchamber array the surfaces of which have hydrophobicity; irradiating the storage sections with excitation light; and detecting the fluorescence reaction of the sample with an image sensor for each of the storage sections, wherein the step of filling the hydrophilic solvent includes the steps of causing the hydrophilic solvent to flow from the openings of the storage sections; and occluding the openings with a hydrophobic solvent.

Advantageous Effects of Invention

According to the present invention, the openings of the storage sections are sealed up with a hydrophobic solvent to confine the hydrophilic solvent containing a biological sample in the storage sections. Consequently, it is possible to prevent the concentrations of the biological sample and the reagent contained in the storage sections from becoming lower, and thereby upgrade measurement sensitivity.

BRIEF DESCRIPTION OF DRAWINGS

FIGS. 2A to 2C are plan views respectively illustrating the configurations of an image sensor and a microchamber array in the detector according to the first embodiment, whereas FIG. 2A is a plan view of the image sensor, FIG. 2B is a plan view of the microchamber array, and FIG. 2C is a plan view in which the microchamber array is overlaid on the image sensor;

FIGS. 3A to 3F are perspective views illustrating a method for manufacturing the detector according to the first embodiment in a stepwise manner, wherein FIG. 3A is a drawing illustrating a step of fixing an Si substrate on the image sensor, FIG. 3B is a drawing illustrating a step of forming an Al film and a resist on the Si substrate, FIG. 3C is a drawing illustrating a step of forming a pattern in the resist, FIG. 3D is a drawing illustrating a step of forming through-holes in the Al film, FIG. 3E is a drawing illustrating a step of forming through-holes in the Si substrate, and FIG. 3F is a drawing illustrating a step of removing the resist and the Al film;

FIGS. 4A to 4D are perspective views illustrating a method for manufacturing the detector according to the first embodiment in a stepwise manner, wherein FIG. 4A is a drawing illustrating a step of forming an Al pattern on the back surface of the image sensor, FIG. 4B is a drawing illustrating a step of performing outer shape processing, FIG. 4C is a drawing illustrating a step of fixing the detector on a polyimide substrate, and FIG. 4D is a drawing illustrating a step of covering the detector with resin;

FIGS. 5A to 5C are cross-sectional views illustrating a state in use of the detector according to the first embodiment, wherein FIG. 5A is a drawing illustrating a step of introducing a hydrophilic solvent to the microchamber array, FIG. 5B is a drawing illustrating a step of filling the storage sections with the hydrophilic solvent, and FIG. 5C is a drawing illustrating a step of sealing up the openings with a hydrophobic solvent;

FIGS. 7A and 7B are drawings illustrating incident angles of excitation light and images detected by the image sensor in the detector according to the first embodiment, wherein FIG. 7A shows a case where the incident angle is 0° and FIG. 7B shows a case where the incident angle is 45°;

FIGS. 9A to 9D are drawings illustrating the results of detection using the detector according to the first embodiment, wherein FIG. 9A is an image when the microchamber array is observed from thereabove with a microscope, FIG. 9B is the result of detection with the image sensor after a lapse of 10 minutes, FIG. 9C is the result of detection with the image sensor after a lapse of 30 minutes, and FIG. 9D is the result of detection with the image sensor after a lapse of 60 minutes;

FIGS. 10A and 10B are graphs illustrating the relationship between detection time and detection results of the detector according to the first embodiment, wherein FIG. 10A is the result of measuring detected intensity using the detector and FIG. 10B is the result of detecting the concentration of a fluorescent dye using a conventional optical microscope; and FIGS. 11A to 11C are cross-sectional views illustrating a detector according to a second embodiment, wherein FIG. 11A is a drawing illustrating a state before use, FIG. 11B is a drawing illustrating a state of use (1), and FIG. 11C is a drawing illustrating state of use (2).

DESCRIPTION OF EMBODIMENTS

First Embodiment

Hereinafter, embodiments of the present invention will be described in detail with reference to the accompanying drawings.

Figure 1:
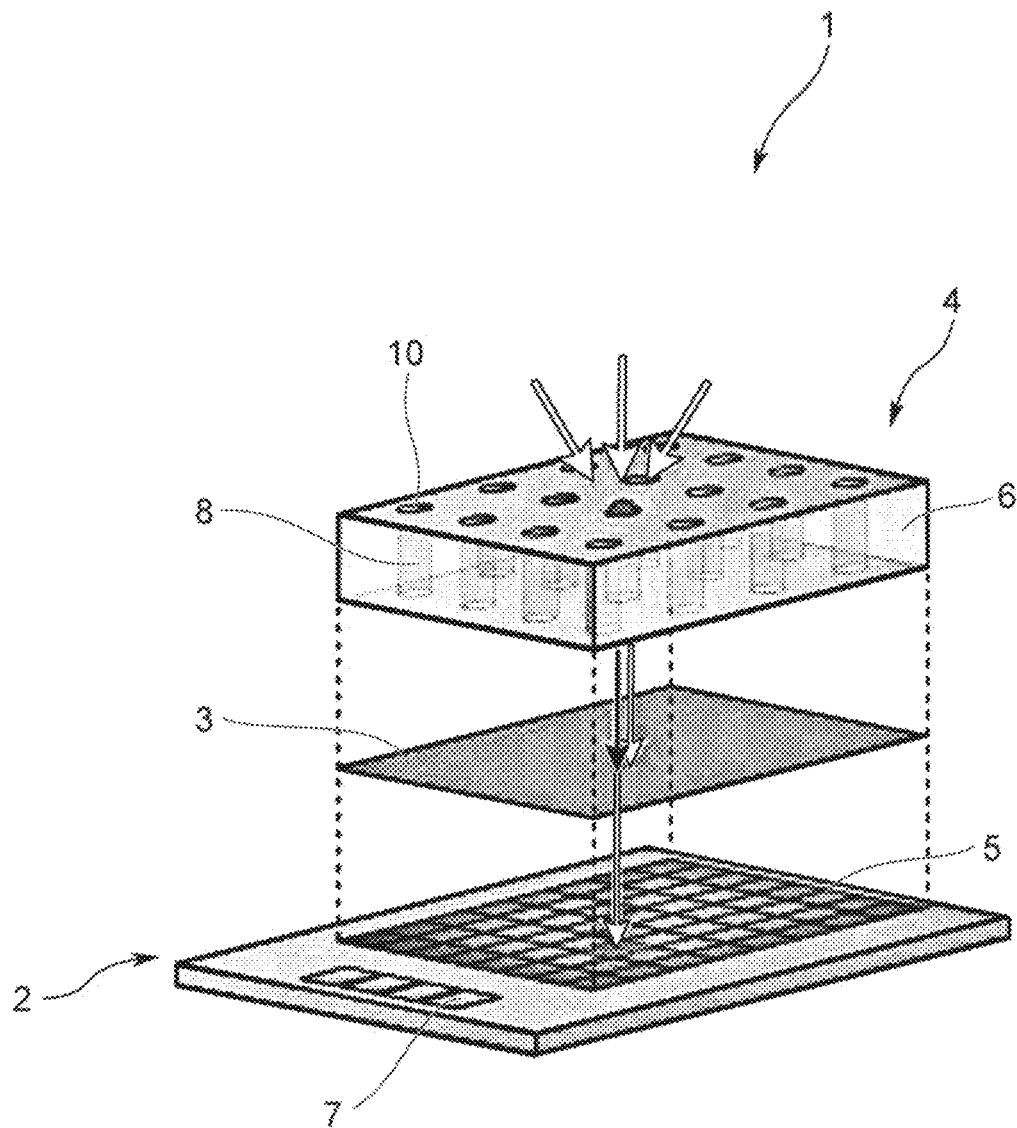
FIG. 1 is an exploded perspective view of the overall configuration of a detector according to a first embodiment.

A detector 1 illustrated in FIG. 1 is provided with an image sensor 2, an interference filter 3, and a microchamber array 4. The detector 1 stores a hydrophilic solvent 42 containing a biological sample in the microchamber array 4 and detects the fluorescence reaction of the biological sample with the image sensor 2.

In the case of the present embodiment, biological samples refer to, for example, biological molecules or virus particles, such as protein, antibodies or nucleic acid, which react with reagents. As reagents, it is possible to use, for example, FDG (fluorodeoxyglucose) and beads.

Beads are preferably 1 μm to 4 μm in average particle diameter. By decreasing the average particle diameter of beads, it is possible to efficiently confine beads in the microchamber array 4 and achieve the high densification of the microchamber array 4. Note that "average particle diameter" refers here to a numerical value measured by means of electron microscope observation or a dynamic light scattering method.

In the case of the present embodiment, the detector 1 is equipped with the microchamber array 4 disposed on the image sensor 2 through the interference filter 3. As the image sensor 2, a CMOS sensor, for example, can be used. The image sensor 2 includes a plurality of picture elements 5 having a predetermined size formed therein and bonding pads 7 disposed therein. The interference filter 3 is firmly bonded onto the picture elements 5 of the image sensor 2 with an adhesive agent to prevent excitation light radiated to the microchamber array 4 from entering the picture elements 5 of the image sensor 2.

The microchamber array 4 includes a chamber body 6 composed of a plate-like member formed from, for example, glass, silicon or polymeric resin, and a plurality of storage sections 8 formed in the chamber body 6. The surfaces of the chamber body 6 preferably have hydrophobicity. Hydrophobicity is the same in meaning as lipophilicity and signifies that affinity with a hydrophobic solvent 44 is higher than affinity with the hydrophilic solvent 42. In this case, water-repellent resin or fluorine-based polymeric resin, for example, can be used for the surfaces of the chamber body 6. As the fluorine-based polymeric resin, it is possible to suitably use amorphous fluorine resin or the like which has high hydrophobicity and low toxicity to biological samples. As the amorphous fluorine resin, it is possible to select the resin from the group consisting of, for example, CYTOP (registered trademark), TEFLON (registered trademark) AF2400, and TEFLON (registered trademark) AF1600.

The storage sections 8 are through-holes bored from a surface of the chamber body 6 in the thickness direction thereof. The volumetric capacity of each storage section 8 is preferably of a femtoliter class, since the concentrations of a biological sample and a reagent need to be made sufficiently high, in order to allow the reagent and the biological sample to efficiently react with each other.

Figures 2A, 2B:
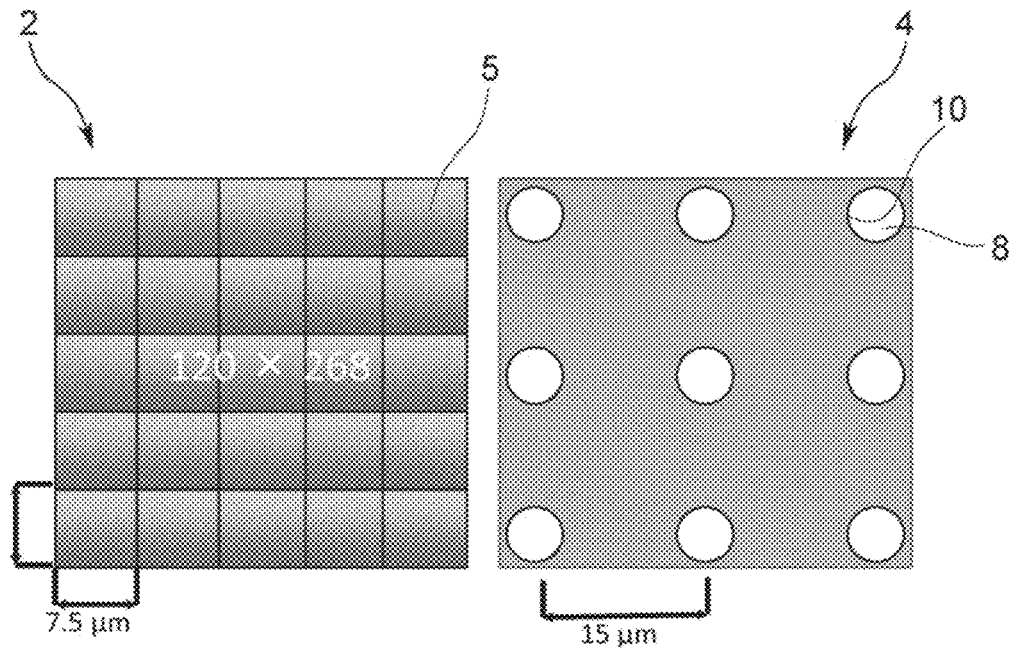

As illustrated in FIG. 2A, the image sensor 2 includes a plurality of continuously-arranged picture elements 5 having a predetermined size. In the case of the present embodiment, the image sensor 2 includes a plurality of square picture elements 5, the length of one side of which is 7.5 μm.

As illustrated in FIG. 2B, the microchamber array 4 includes the storage sections 8 continuously arranged at predetermined intervals. The interval is set to be a length at which incoming excitation light can be cut off. In the case of the present embodiment, the microchamber array 4 includes a plurality of storage sections 8 formed at 15 μm intervals.

Figure 2C:
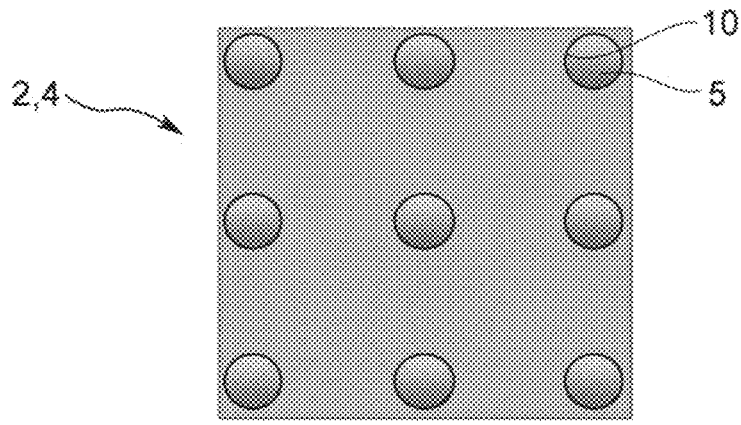

As illustrated in FIG. 2C, the microchamber array 4 is fixed onto the image sensor 2, so that one storage section 8 corresponds in position to one picture element 5.

A shield material containing a black dye, though not illustrated in the figure, is preferably applied on sidewalls between the interference filter 3 and the microchamber array 4, and between the interference filter 3 and the image sensor 2. Consequently, it is possible to prevent excitation light from entering the picture elements 5 of the image sensor 2 from gaps between the interference filter 3 and the microchamber array 4, and between the interference filter 3 and the image sensor 2.

Figure 3A:
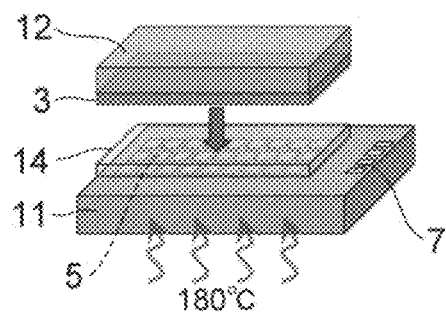

Next, a description will be made of a method for manufacturing the detector 1 according to the present embodiment. First, an adhesive agent (CYTOP (registered trademark) in the case of the present embodiment) 14 is applied on the picture elements 5 of a 150 μm-thick image sensor 11 at a thickness of 2 μm. Then, a 60 μm-thick Si substrate 12, on one surface of which a 3 μm-thick interference filter 3 is disposed, is fixed to the image sensor 11 through the interference filter 3, while heating the substrate at 180° C., with a surface of the interference filter 3 overlaid on the adhesive agent 14 (FIG. 3A).

Figure 3D:
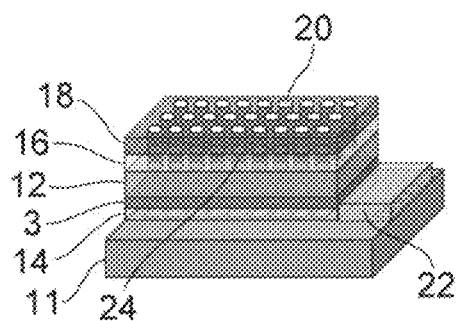
Figure 3B:
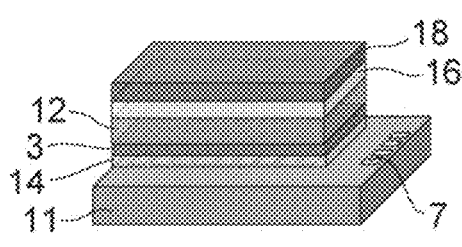

Subsequently, a 200 nm-thick Al film 16 is formed on the Si substrate 12 by an evaporation method, and a resist 18 is provided on the Al film 16 (FIG. 3B).

Figure 3E:
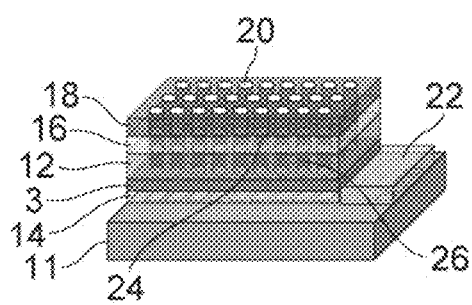
Figure 3C:
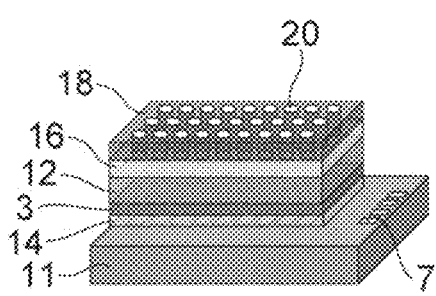

Then, a pattern is formed in the resist 18 and throughholes 20 are bored therein (FIG. 3C). After a thick-film resist 22 for protecting a bonding pad section 7 is formed, throughholes 24 are formed in the Al film 16 by wet etching (FIG. 3D).

Figure 3F:
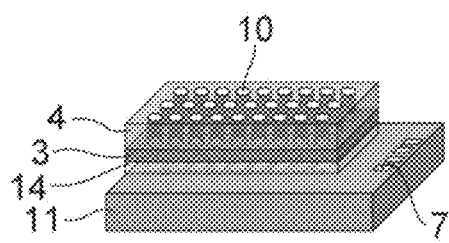

In addition, through-holes 26 are formed in the Si substrate 12 by dry etching (Deep Reactive Ion Etching: DRIE) (FIG. 3E). Then, the resist 18 and the Al film 16 are removed using mixed acid (acetic acid, phosphoric acid, nitric acid, and pure water (volume ratio=4:4:1:1)) (FIG. 3F).

Figure 4A:
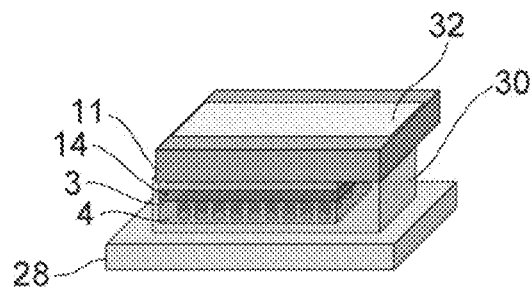
Figure 4B:
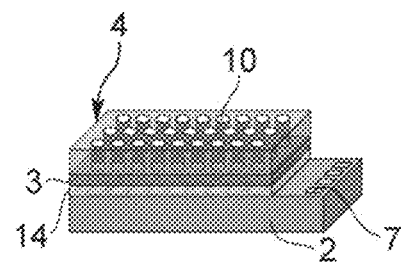

Subsequently, after a thick-film resist 30 disposed on a glass substrate 28 for protecting the bonding pad section 7 is formed, an Al pattern 32 is formed on the back surface of the image sensor 11 (FIG. 4A), and then subjected to outer shape processing with DRIE. The detector 1 can thus be obtained (FIG. 4B).

Figure 4C:
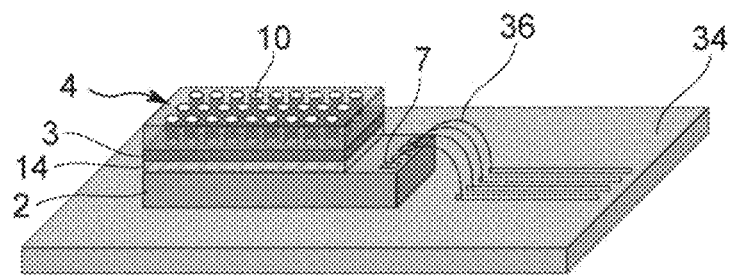

The detector 1 thus formed is fixed on a polyimide substrate 34 and wire-bonded at the bonding pad section 7 (FIG. 4C).

Figure 4D:
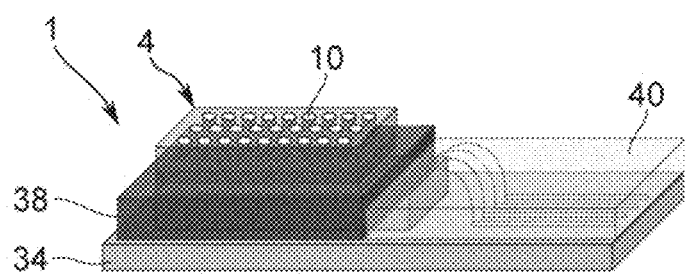

Bonding wires 36 and the bonding pad section 7 are covered with epoxy resin 40. In addition, a shield material 38 containing a black dye is disposed between the interference filter 3 and the microchamber array 4, and between the interference filter 3 and the image sensor 2 (FIG. 4D).

Next, a description will be made of the operation and advantageous effects of the detector 1 configured as described above. First, a hydrophilic solvent 42 containing a biological sample and a reagent is introduced into the storage sections 8 of the microchamber array 4 (FIG. 5A). As the hydrophilic solvent 42, it is possible to use at least one solvent selected from the group consisting of, for example, water, hydrophilic alcohol, hydrophilic ether, ketone, nitrile-based solvent, dimethyl sulfoxide (DMSO), and N, N-dimethylformamide (DMF), or a mixture or the like containing this solvent.

Subsequently, the detector 1 is left to stand in a reducedpressure environment to deaerate the detector. Consequently, air inside the storage sections 8 can be removed to efficiently introduce the hydrophilic solvent 42 containing the biological sample into the storage sections 8 (FIG. 5B).

Figure 5C:
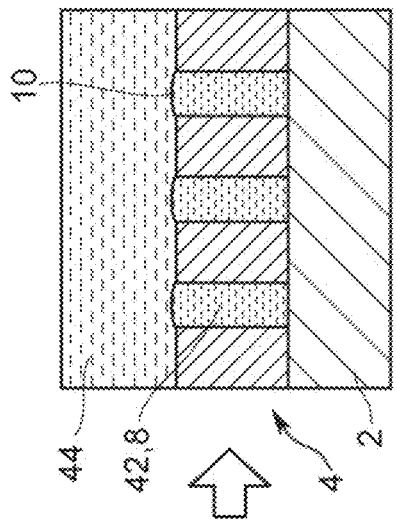
Figure 5B:
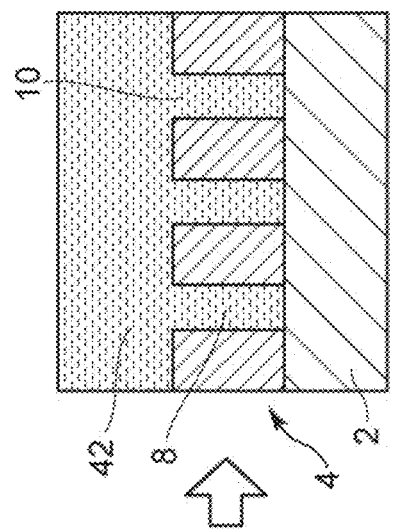
Figure 5A:
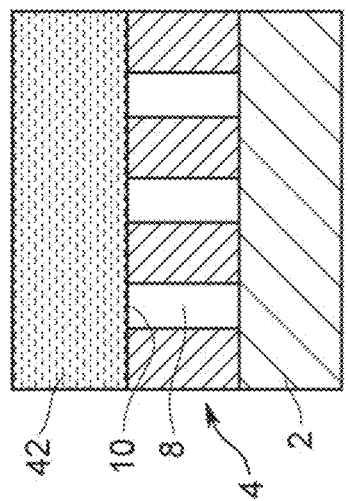

Then, a hydrophobic solvent 44 is introduced to the periphery of the openings 10 of the storage sections 8 (FIG. 5C). The hydrophobic solvent 44 may be any solvent immiscible with the hydrophilic solvent 42. It is therefore possible to suitably use at least one solvent selected from the group consisting of, for example, saturated hydrocarbon, unsaturated hydrocarbon, aromatic hydrocarbon, silicone oil, perfluorocarbon, halogen-based solvent, and hydrophobic ionic liquid, or a mixture or the like containing this solvent.

By introducing the hydrophobic solvent 44 to the periphery of the openings 10 of the storage sections 8, a liquid droplet covered with the hydrophobic solvent 44 is formed in each storage section 8. The biological sample can thus be sealed in the storage section 8. Consequently, it is possible to seal the biological sample in the storage sections 8 of a femtoliter class.

Figure 6:
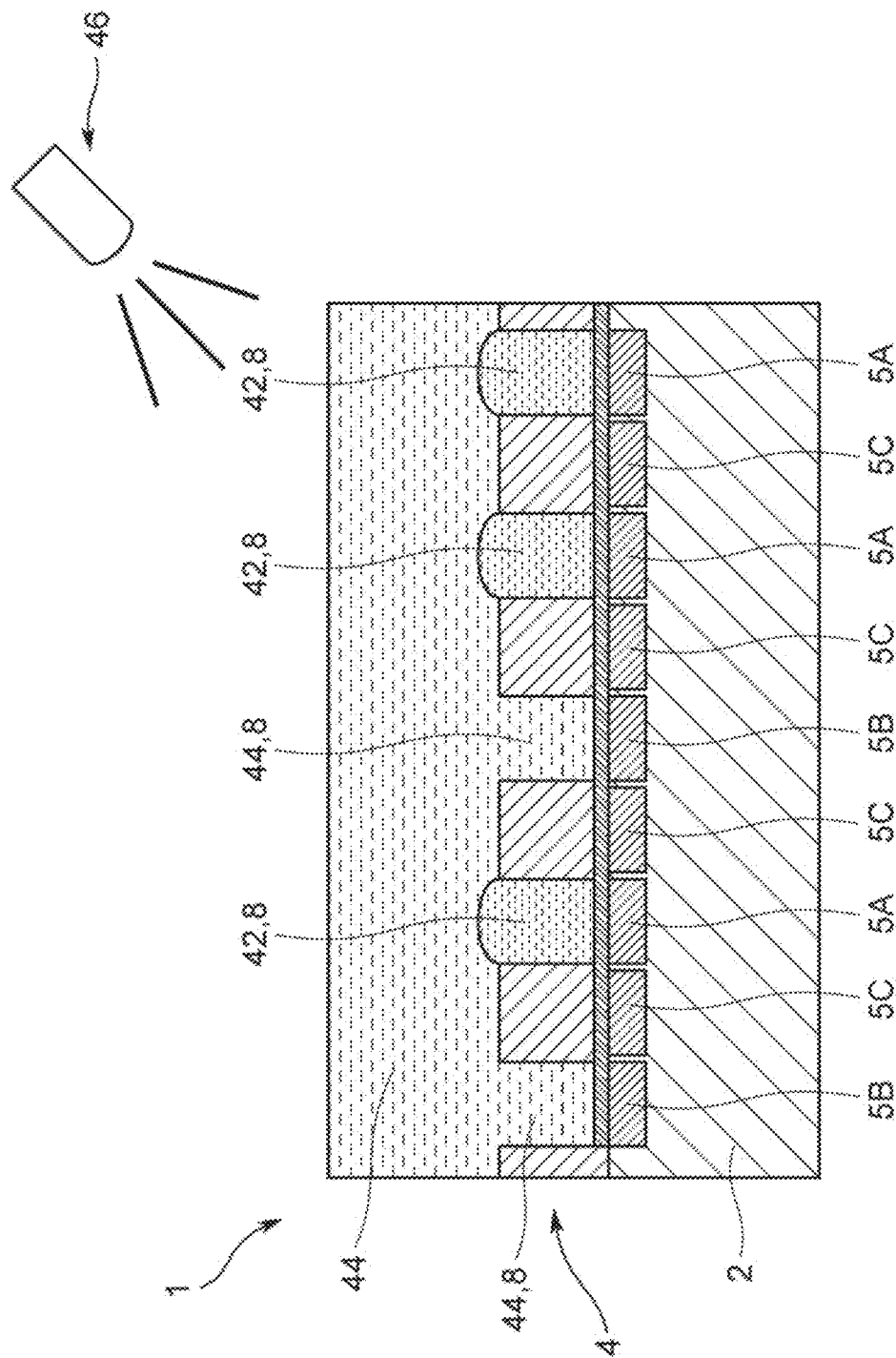
FIG. 6 is a drawing illustrating a state in use of the detector according to the first embodiment.

Subsequently, excitation light is radiated to the microchamber array 4 of the detector 1 from a light source 46 (FIG. 6). A fluorescent substrate is decomposed by a predetermined enzyme combined with the biological sample and a fluorescent substance becomes liberated. This fluorescent substance is detected with a picture element 5A corresponding in position to each storage section 8 through the interference filter 3. On the other hand, the fluorescent substance is not detected at picture elements 5B corresponding in position to storage sections not filled with the hydrophilic solvent and picture elements 5C corresponding in position to spaces between the storage sections.

As described above, the detector 1 seals up the openings 10 of the storage sections 8 with the hydrophobic solvent 44 and confines the hydrophilic solvent 42 containing the biological sample in the storage sections 8. Consequently, it is possible to prevent the concentrations of the biological sample and the reagent contained in the storage sections 8 from becoming lower, and thereby upgrade measurement sensitivity.

In addition, the detector 1 can detect the number of storage sections 8 in which the reagent is contained and the number of storage sections 8 in which portions of the reagent having captured the biological sample are contained, and calculate the ratio of the number of portions of the reagent, among the total number of portions of the reagent, which have captured a target molecule. Consequently, it is possible to quantify the concentration of the target molecule.

In addition, in the case of the present embodiment, the image sensor 2 can detect whether or not a portion of the reagent is present in each storage section 8 and whether a portion of the reagent having captured the biological sample is contained in each storage section 8, at a picture element 5 corresponding in position to each storage section 8. Consequently, the present embodiment does not require any optical microscopes that have been necessary conventionally. It is therefore possible to downsize a detection system and speed up detecting operation.

Next, a description will be made of evaluations conducted using an actually-manufactured detector 1. A microchamber array 4 of the manufactured detector 1 is formed so that the thickness thereof is 60 μm, the effective length of each storage section 8 is 4 μm, and the interval between storage sections 8 is 15 μm. As the image sensor 2, a CMOS sensor having a chip size of 1.2 mm×3.6 mm is used, where the length of one side of each picture element 5 is 7.5 μm, and the array size of the sensor is 120×268.

First, a verification was made of an appropriate incident angle of excitation light. For excitation light, there was used blue light selected out of white light from a mercury lamp with a blue interference filter (transparent center wavelength: 469 nm, wavelength width: 35 nm). The excitation light to be radiated to the microchamber array 4 is preferably obliquely radiated to the openings 10 of the storage sections 8 from thereabove, as illustrated in FIGS. 7A and 7B. That is, the excitation light, if vertically radiated to the openings 10 of the storage sections 8, directly enters the picture elements 5 of the image sensor 2. In contrast, if the excitation light is obliquely radiated to the openings 10 of the storage section 8 from thereabove as illustrated in FIG. 7B, the image sensor 2 does not detect the excitation light. It is therefore possible to more securely detect a fluorescent substance.

Figure 8:
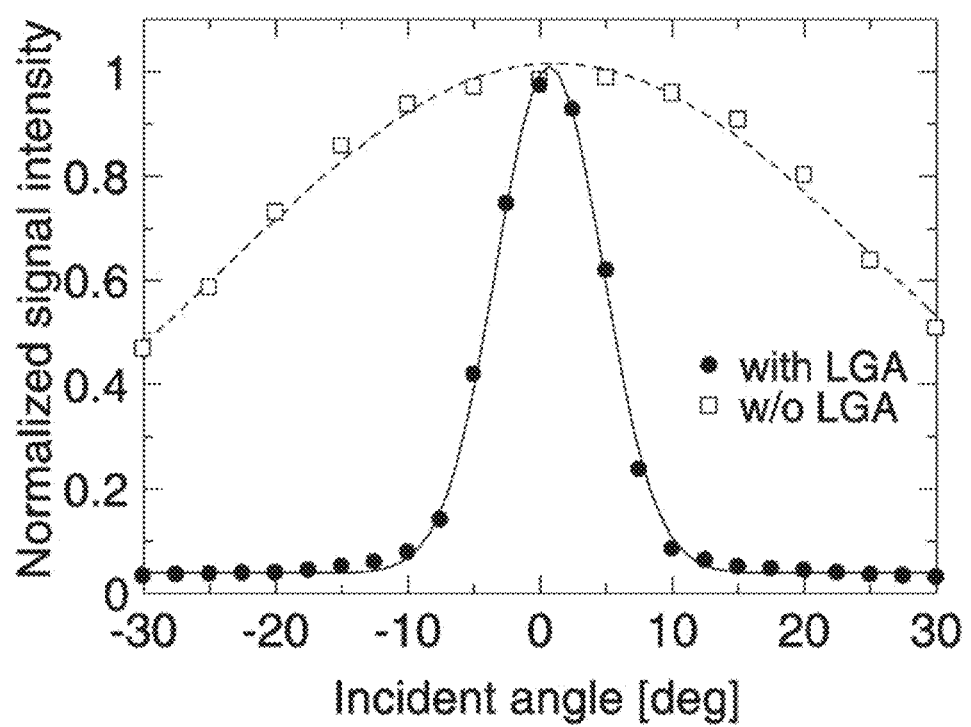
FIG. 8 is a graph illustrating the relationship between the incident angle of excitation light and intensity detected at the image sensor in the detector according to the first embodiment.

FIG. 8 is a graph illustrating the relationship between the incident angle of excitation light and intensity detected at the image sensor 2, where ● indicates results obtained in the presence of the microchamber array 4 and □ indicates the results obtained in the absence of the microchamber array 4. The incident angle refers to an angle formed by an axis extending in a vertical direction and an axis parallel with a direction in which the excitation light enters, where the vertical direction is defined as 0°. From these results, it has been confirmed that varying the incident angle enables the microchamber array 4 to cut off the excitation light.

FIGS. 9A to 9D are drawings illustrating results of detection by the detector 1 according to the present embodiment. Note that a phosphate buffer solution was used as the hydrophilic solvent 42, β-gal (β-galactosidase: 10 nM) was used as the biological sample, and FDG (4 mM) was used as the reagent.

Figure 9A:
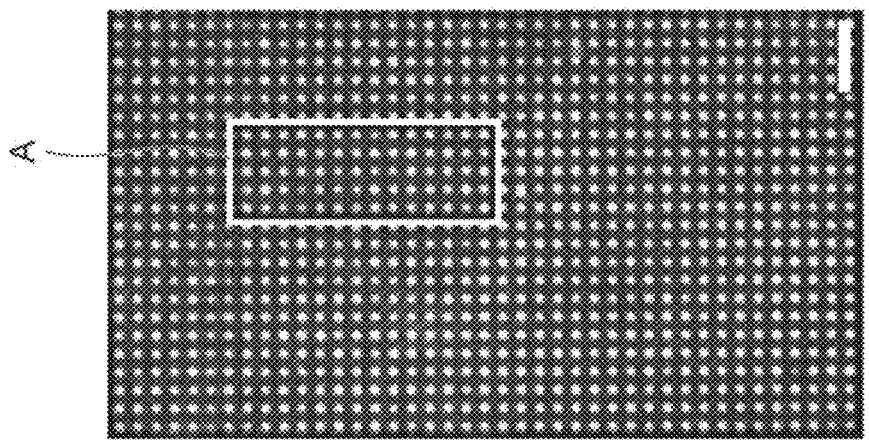

FIG. 9A is an image when the microchamber array 4 is observed from thereabove with a microscope. Since each storage section 8 shines brightly, it is confirmed that a portion of the biological sample having reacted with the reagent is contained in each storage section 8.

Figure 9B:
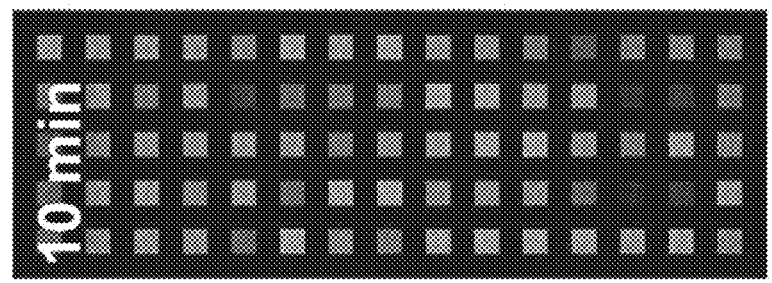
Figure 9C:
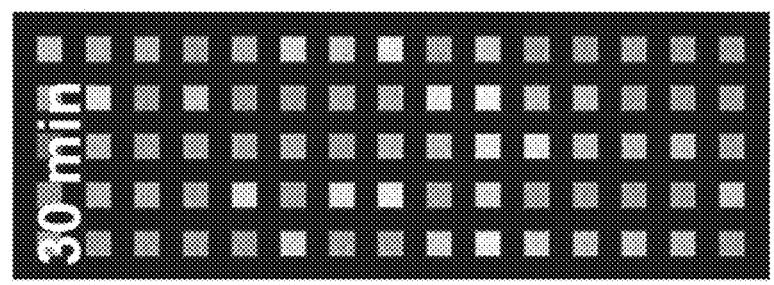
Figure 9D:
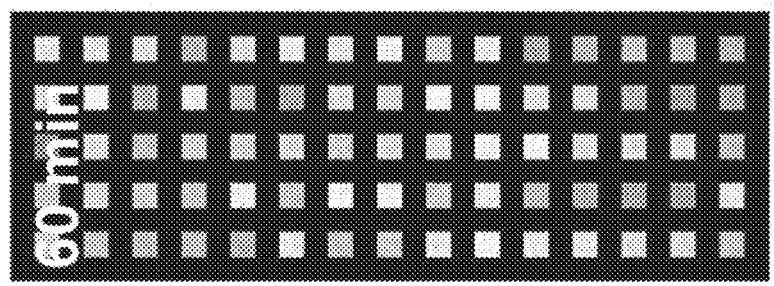

FIGS. 9B to 9D illustrate results of detection by the detector 1 in the area A of FIG. 9A. It was confirmed that the number of picture elements 5 having detected a fluorescence reaction increased as the fluorescence reaction progressed along with the lapse of time.

Figure 10A:
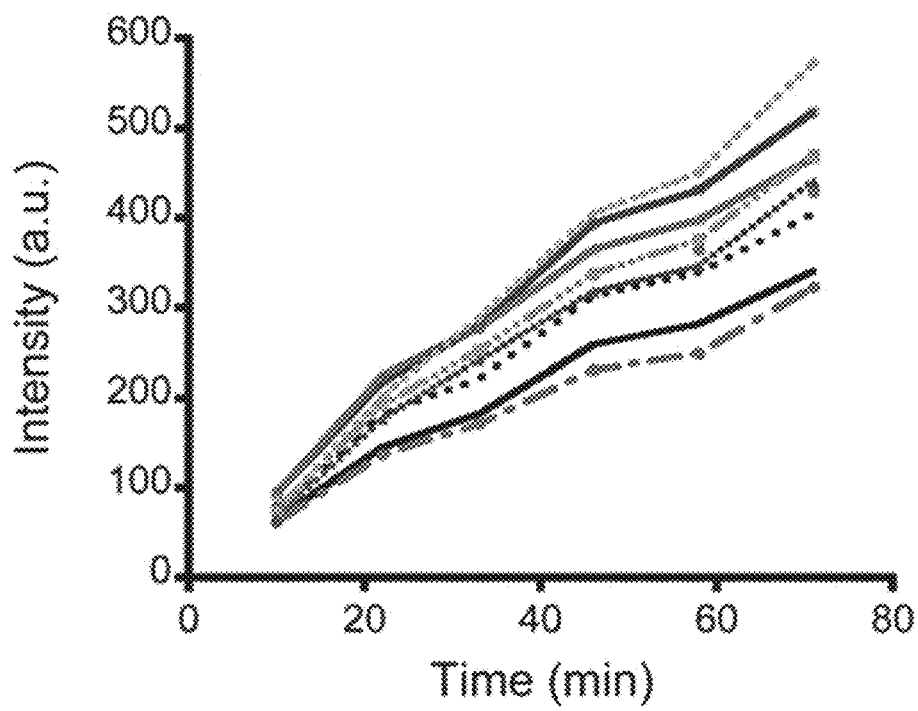
Figure 10B:
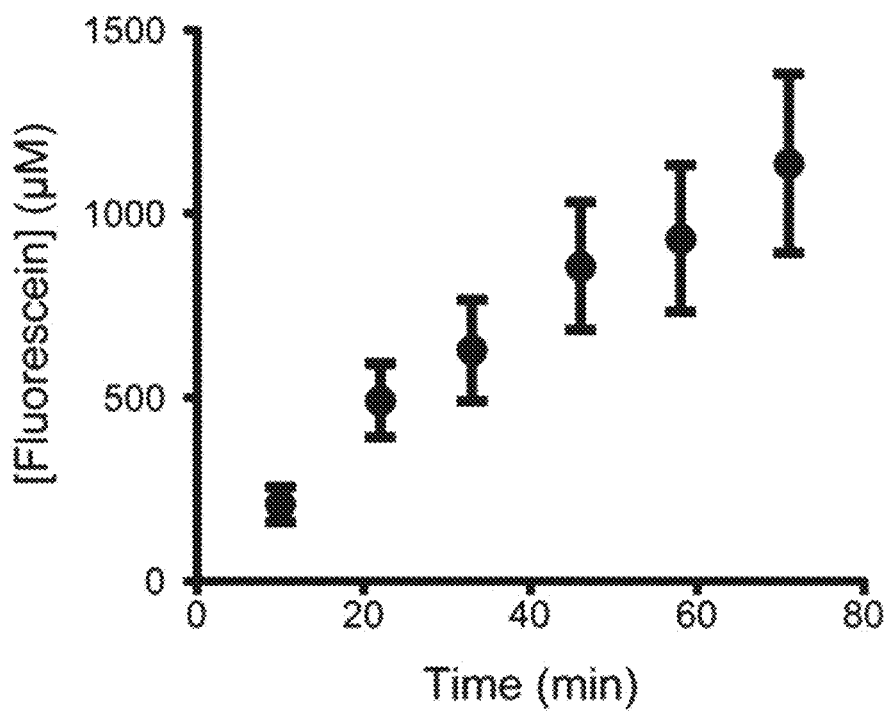

FIG. 10A is a graph illustrating the relationship between the detection time of the detector 1 and detected intensity. From this result, it has been confirmed that detection results favorably comparable to results obtained with a conventional optical microscope (FIG. 10B) are obtained with the detector 1 according to the present embodiment.

Second Embodiment

Figure 11A:
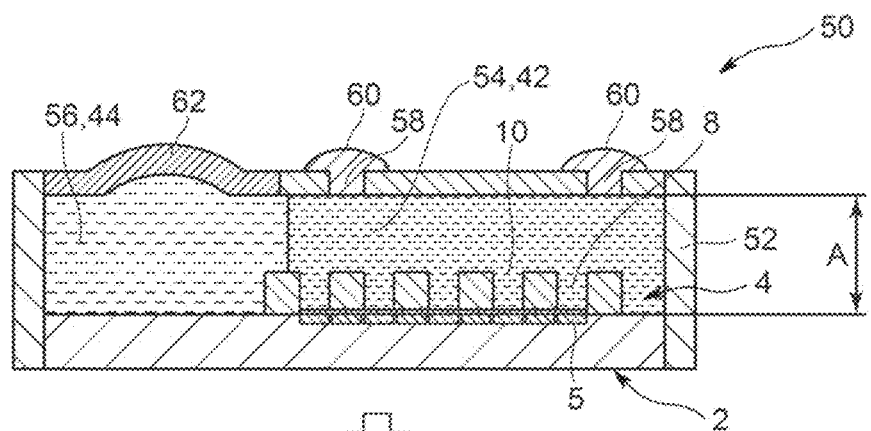
Figure 11B:
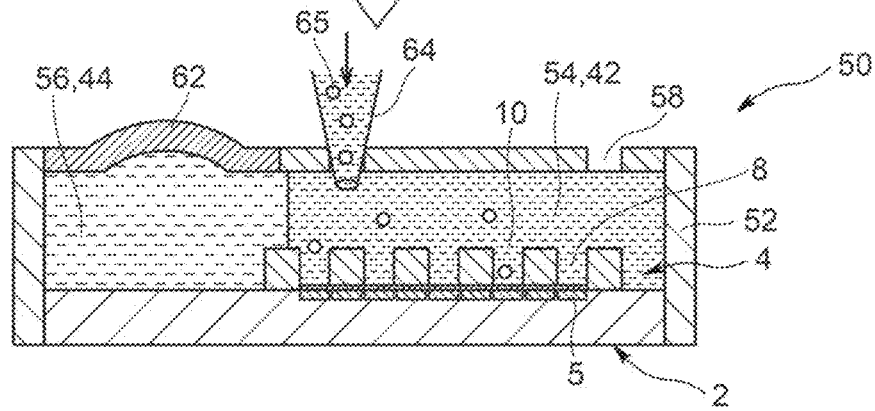
Figure 11C:
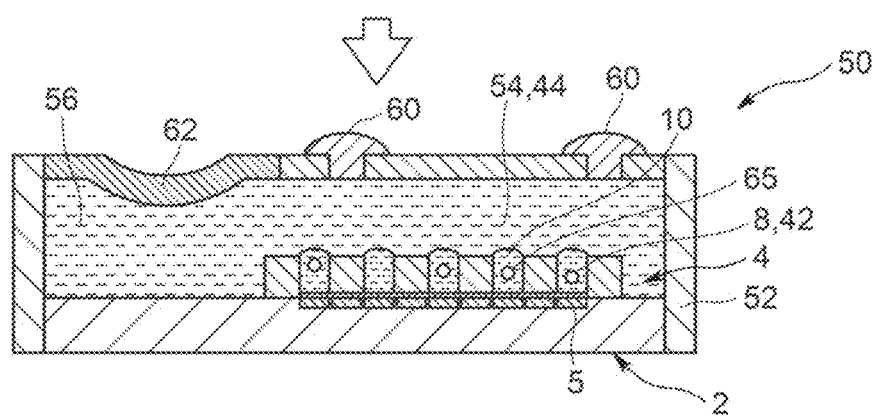

Next, a detector 1 according to a second embodiment of the present invention will be described with reference to FIGS. 11A to 11C. Constituent elements which are the same as those of the first embodiment are denoted by like reference numerals and will not be described any further for the sake of simplification.

A detector 50 illustrated in the figure is provided with an image sensor 2, an interference filter 3 (not illustrated in the figure), a main unit 52, and a microchamber array 4.

The main unit 52 is composed of a tubular member which is open at the bottom surface thereof and the upper surface of which is closed. The image sensor 2 is disposed so as to occlude the opening of the bottom surface of the main unit 52. A flow channel 54 is formed on the microchamber array 4 disposed on the image sensor 2. The flow channel 54 is in communication with each storage section 8 of the microchamber array 4 through the opening 10 of the storage section. The flow channel 54 and all of the storage sections 8 are filled with a hydrophilic solvent 42.

A hydrophobic solvent supply unit 56 is disposed at one end of the flow channel 54. A hydrophobic solvent 44 is stored in the hydrophobic solvent supply unit 56. A deformable part 62 elastically deformable by an external force is provided on the upper surface of the main unit 52 of the hydrophobic solvent supply unit 56.

A pair of through-holes 58 through which the flow channel 54 is in communication with the outside is provided on the upper surface of the main unit 52, and covers 60 for closing the through-holes 58 are attachably and detachably disposed on the upper surface. An internal height A of the main unit 52 is preferably equal to or smaller than the size of an oil droplet of the hydrophobic solvent 44. By setting the internal height A equal to or smaller than the size of the oil droplet, the hydrophobic solvent 44 and the hydrophilic solvent 42 are held in a state of being separated from each other without mixing with each other, as illustrated in the figure. Accordingly, any members for dividing off the flow channel 54 and the hydrophobic solvent supply unit 56 from each other are not required in the boundary between the flow channel 54 and the hydrophobic solvent supply unit 56. Under normal conditions, the size of the oil droplet stable in water is on the order of 100 μm. The internal height A is, therefore, preferably 100 μm or less.

Next, a description will be made of the operation and advantageous effects of the detector 50 configured as described above. First, the covers 60 are removed and the hydrophilic solvent 42 containing a biological sample and a reagent 65 is introduced into the flow channel 54 from one of the through-holes 58, as illustrated in FIG. 11B. Consequently, the reagent 65 is contained in each storage section 8.

Next, a force is externally applied to the deformable part 62 of the hydrophobic solvent supply unit 56 to elastically deform the deformable part 62. This force causes the hydrophobic solvent 44 stored in the hydrophobic solvent supply unit 56 to flow into the flow channel 54. Thus, it is possible to form a liquid droplet covered with the hydrophobic solvent 44 in each storage section 8 and seal the biological sample in the storage section 8.

The detector 50 according to the present embodiment allows the biological sample to be sealed in the storage sections 8 with a single stroke, after the hydrophilic solvent 42 containing the biological sample and the reagent 65 is introduced. Since the preliminary work of causing the hydrophobic solvent 44 to flow in can thus be skipped, it is possible to further simplify inspection tasks.

Note that in the present embodiment, a case has been cited in which any members for dividing off the flow channel 54 and the hydrophobic solvent supply unit 56 from each other are not present in the boundary therebetween. The present invention is not limited to this embodiment, however. For example, a bulkhead may be disposed in the boundary between the flow channel 54 and the hydrophobic solvent supply unit 56. The bulkhead is formed so as to be breakable by a force applied to the deformable part 62.

Consequently, the hydrophobic solvent 44 is securely retained in the hydrophobic solvent supply unit 56 by the bulkhead at the stage of the hydrophilic solvent 42 containing the biological sample and the reagent 65 having been introduced into the flow channel 54. Then, applying a force to the deformable part 62 causes the force to be transferred to the bulkhead through the hydrophobic solvent 44 stored in the hydrophobic solvent supply unit 56. When the bulkhead breaks due to the force thus transferred, the hydrophobic solvent 44 stored in the hydrophobic solvent supply unit 56 flows into the flow channel 54. Thus, it is possible to form a liquid droplet covered with the hydrophobic solvent 44 in each storage section 8 and seal the biological sample in the storage section 8.

By disposing the bulkhead in the boundary between the flow channel 54 and the hydrophobic solvent supply unit 56 in this way, it is possible to more securely prevent the hydrophobic solvent 44 from entering the flow channel 54 at the stage of the hydrophilic solvent 42 containing the biological sample and the reagent 65 having been introduced into the flow channel 54, i.e., at the stage of the reagent 65 being contained in each storage section 8. Consequently, it is possible to improve the certainty of operation.

Modified Example

The present invention is not limited to the above-described embodiments, but may be modified as appropriate within the scope of the subject matter of the present invention.

Although in the second embodiment, a case has been cited in which the pair of through-holes 58 is disposed, the present invention is not limited to this embodiment. Alternatively, there may be only one through-hole 58.

REFERENCE SIGNS LIST

1: Detector
2: Image sensor
4: Microchamber array
5: Picture element
8: Storage section
10: Opening
42: Hydrophilic solvent
44: Hydrophobic solvent
54: Flow channel
56: Hydrophobic solvent supply unit
58: Through-hole
62: Deformable part

The invention claimed is:

1. A detector, comprising:
an image sensor that includes picture elements;
a side wall that surrounds a periphery of the image sensor, extending from the image sensor;
a top plate that is disposed at an upper edge of the side wall and extends in parallel to the image sensor, so that an internal storage space is formed by the top plate, the image sensor, and the side wall so as to keep an internal height between the top plate and the image sensor, wherein the internal storage space is segmented into an array region and a hydrophobic solvent storage region, the array region communicating with the hydrophobic solvent storage region;
a microchamber array that is disposed on the image sensor in the array region, and includes a plurality of storage sections to be filled with a hydrophilic solvent containing a biological sample, wherein the storage sections are arranged corresponding to the picture elements of the image sensor,
wherein the top plate includes:
a pair of through holes above the array region, one of which is arranged close to the hydrophobic solvent storage region and defined as an inner hole, and the other one of which is arranged opposite to the hydrophobic solvent storage region across the inner hole and defined as an outer hole; and
a deformable part above the hydrophobic solvent storage region, wherein the deformable part is formed of an elastic material and deformed toward the image sensor by an external force such that the hydrophobic solvent stored in hydrophobic solvent storage region is discharged into the array region by the external force.

2. The detector according to claim 1, further comprising a partition wall provided at a boundary of the array region and the hydrophobic solvent storage region, wherein the partition wall is breakable by the hydrophobic solvent discharged from the hydrophobic solvent storage into the array region by the external force.

3. The detector according to claim 1, further comprising a first detachable cover that is capable of closing the inner hole.

4. The detector according to claim 1, further comprising a second detachable cover that is capable of closing the outer hole.

5. The detector according to claim 1, further comprising a light source that emits excitation light to the microchamber array along a direction inclined from the normal to the microchamber array.

6. The detector according to claim 5, wherein the light source includes a mercury lamp and a blue interference filter having a transparent center wavelength of 469 nm and a wavelength width of 35 nm.

7. The detector according to claim 1, wherein the internal height is 100 μm or less.

8. The detector according to claim 1, wherein the volumetric capacity of each one of the storage sections is of a femtoliter class.

9. A detection method using the detector according to claim 1, comprising the steps of:
injecting the hydrophilic solvent containing the biological sample into the array region through either one of the inner hole and the outer hole, thereby to allow plurality of storage sections of the microchamber array to be filled with the hydrophilic solvent;
supplying the hydrophobic solvent from the hydrophobic solvent storage region into the array region by applying an external force to the deformable part, thereby to occlude the storage sections with the hydrophobic solvent; and
observing the biological sample in the storage sections with the corresponding picture elements of the image sensor.

10. A detection method using the detector according to claim 5, comprising the steps of:
injecting the hydrophilic solvent containing the biological sample into the array region through either one of the inner hole and the outer hole, thereby to allow plurality of storage sections of the microchamber array to be filled with the hydrophilic solvent;
supplying the hydrophobic solvent from the hydrophobic solvent storage region into the array region by applying an external force to the deformable part, thereby to occlude the storage sections with the hydrophobic solvent;
irradiating the microchamber array with the excitation light from the light source; and
observing a fluorescence reaction of the biological sample under the excitation light in the storage sections with the corresponding picture elements of the image sensor.

11. The detection method according to claim 10, wherein a mercury lamp and a blue interference filter are used to irradiate the microchamber array with the excitation light in the steps of irradiating and observing.

12. The detection method according to claim 10, wherein the excitation light is radiated to the microchamber array along a direction inclined from the normal to the microchamber array in the steps of irradiating and observing.

13. The detection method according to claim 9, further comprising the step of:
reducing a pressure of an environment above the microchamber array, following the step of injecting, thereby to facilitate allowing the plurality of storage sections of the microchamber array to be filled with the hydrophilic solvent.

14. The detection method according to claim 10, further comprising the step of:
reducing a pressure of an environment above the microchamber array, following the step of injecting, thereby to facilitate allowing the plurality of storage sections of the microchamber array to be filled with the hydrophilic solvent.

* * * * *